("(12) United States Patent" block)

(12) United States Patent
Arab et al.

(10) Patent No.: US 7,335,750 B2
(45) Date of Patent: *Feb. 26, 2008

(54) HYBRID COMPOSITIONS FOR INTRACELLULAR TARGETING

(75) Inventors: Sara Arab, North York (CA); Clifford A. Lingwood, Toronto (CA); Aye-Aye Khine, Concord (CA)

(73) Assignee: Hospital for Sick Children Research and Development Limited Partnership, Toronto, Ontario (CA)

( * ) Notice: Subject to any disclaimer, the term of this patent is extended or adjusted under 35 U.S.C. 154(b) by 612 days.

This patent is subject to a terminal disclaimer.

(21) Appl. No.: 10/298,408

(22) Filed: Nov. 18, 2002

(65) Prior Publication Data

US 2003/0068323 A1    Apr. 10, 2003

Related U.S. Application Data

(63) Continuation of application No. 08/975,953, filed on Nov. 21, 1997, now Pat. No. 6,482,586.

(60) Provisional application No. 60/061,044, filed on Oct. 4, 1997, provisional application No. 60/061,050, filed on Oct. 3, 1997, provisional application No. 60/031,668, filed on Nov. 22, 1996.

(51) Int. Cl.
| | |
|---|---|
| C07K 14/245 | (2006.01) |
| C07H 21/02 | (2006.01) |
| C07H 21/04 | (2006.01) |
| A61K 38/16 | (2006.01) |
| A61K 31/7088 | (2006.01) |
| C12N 5/00 | (2006.01) |
| C12N 15/87 | (2006.01) |
| C12P 21/02 | (2006.01) |

(52) U.S. Cl. .................... 530/402; 530/350; 536/23.1; 536/24.5; 435/69.1; 435/325; 435/455; 435/471; 514/4; 514/44

(58) Field of Classification Search ............... 435/69.7, 435/252.33; 514/4; 424/181.1
See application file for complete search history.

(56) References Cited

U.S. PATENT DOCUMENTS 6,482,586 B1 *  11/2002  Arab et al. ..................... 435/4

OTHER PUBLICATIONS

Khine, AA, Lingwood CA, Capping and receptor-mediated endocytosis of cell-cound verotoxin . . . , 1994 J. Cell. Physiol. 161:319-332.*
Gunzer F, Karch H, Expression of A and B subunits of shiga-like toxin II as fusions with glutathione S-transferase and their potential use in seroepidemiology, 1993, J. Clin. Microbiol. 31:2604-2610.*
Maloney MD, Lingwood CA, CD19 has a potential CD77 (globotriaosyl ceramide)-binding site with sequence similarity to verotoxin B-subunits . . . , 1994, J. Exp. Med. 180:191-201.*
Matsumoto AK, Martin DR,Carter RH, Klickstein LB, Ahearn JM, Fearon DT, Functional dissection of the CD21/CD19/TAPA-1/Leu-13 complex of B lymphocytes, 1993, J. Exp. Med. 178:1407-1417.*
Bradbury LE, Goldmacher VS, Tedder TF, The CD19 signal transduction complex of B lymphocytes: Deletion of the CD19 cytoplasmic domain alters signal transduction but not complex formation with TAPA-1 and Leu 13, 1993, J. Immunol. 151:2915-2927.*
Ramotar K, Boyd B, Tyrrell G, Gariepy J, Lingwood C, Brunton J, Characterization of shiga-like toxin I B subunit purified from overproduction clones of the SLT-I B cistron, 1990, Biochem. J. 272:805-811.*
Fyfe G, Cebra-Thomas JA, Mustain E, Davie JM, Alley CD, Nahm MH, 1987, J. Immunol. 139:2187-2194.*
Duncan RJS, Weston PD, Wrigglesworth R, 1983, Anal. Biochem. 132:68-73.*
BayerEA, Skutelsky E, Wilchek M, The avidin-biotin complex in affinity cytochemistry, 1979, Methods Enzymol. 62:308-315.*
Goding JW, Conjugation of antibodies with fluorochromes: modifications to the standard methods, 1976. J. Immunol. Methods, 13:215-226.*
Sadelain M, Insertional oncogenesis in gene therapy: how much of a risk?, 2004, Gene Therapy 11: 569-573.*
Griesenbach U, Geddes DM, Alton EWFW, Gene therapy for cystic fibrosis: an example for lunch gene therapy, 2004, Gene Therapy 11: S43-S50.*

* cited by examiner

*Primary Examiner*—Sumesh Kaushal
*Assistant Examiner*—Michael Burkhart
(74) *Attorney, Agent, or Firm*—Lahive & Cockfield, LLP; Giulio A. DeConti, Jr.; Cynthis M. Soroos

(57) ABSTRACT

Hybrid compounds comprising a first domain and a second domain are provided. The first domain and the second domain are preferably covalently linked, and the first domain comprises a domain which is capable of specific binding to $Gb_3$; and the second domain comprising a moiety selected from the group consisting of drug moiety, a nucleic acid, a probe, a polypeptide, and a hook, with the proviso that the second domain is not a verotoxin or a fragment thereof. Methods of preparing and using the hybrid compounds are also provided.

14 Claims, 2 Drawing Sheets

HYBRID COMPOSITIONS FOR INTRACELLULAR TARGETING

CROSS-REFERENCE TO RELATED APPLICATIONS

This application is a continuation of Ser. No. 08/975,953, filed Nov. 21, 1997, now U.S. Pat. No. 6,482,586, which claims priority under 35 U.S.C. 119(e) to U.S. provisional application Ser. No. 60/031,668, filed Nov. 22, 1996; No. 60/061,050, filed Oct. 3, 1997; and No. 60/061,044, filed Oct. 4, 1997; the contents of all of which are hereby incorporated by reference.

BACKGROUND OF THE INVENTION

Recent advances in the understanding of the molecular bases of disease states and conditions have permitted the rationally-based development, at least in principle, of therapies which are specifically designed to target a particular molecular entity or entities. Unfortunately, a practical difficulty often arises in attempting to treat diseases with rationally-designed drugs, viz., while the drug may work as expected in vitro, in order to have the desired therapeutic effect the drug must be able to reach the site of action in vivo without being metabolically inactivated or degraded. In the case of drugs which must reach an intracellular site to be effective, providing the drug in a form capable of reaching the desired site can be difficult. Although many proposals have been made to deal with this problem, there are few approaches which are broadly applicable to a wide variety of drugs and disease states. One approach has been to administer the drug in a form, such as a liposome preparation, which allows the drug to cross the cell membrane. However, non-targeted liposomes may deliver the drug to non-target cells or organs, and the use of specifically-targeted liposomes can be expensive or inconvenient.

The endocytotic pathway of many protein toxins comprising separate A (enzymatic) and B (receptor binding) subunits, involves cell binding, internalization, translocation from an intracellular compartment to the cytosol, and enzymatic inactivation of their intracellular targets (1, 2). After translocation to the cytoplasm, the A subunits of ricin, abrin, modeccin, and verotoxins catalytically inactivate the 28 S RNA of 60 S ribosomal subunits, leading to an inhibition of cellular protein synthesis (3, 4). In addition, both the holotoxin and the B subunit are capable of inducing programmed cell death (apoptosis) (5-7).

The *E coli* derived family of verotoxins (or Shiga-like toxins) comprise VT1, VT2 and VT2c, which are involved in the etiology of microvascular disease in man (8), primarily in the very young and elderly (9), and VT2e which causes edema disease in pigs (10). The glycolipid globotriaosylceramide (gala1-4galb1-4glc cer.-$Gb_3$) at the plasma membrane is the specific receptor for all verotoxins and mediates the internalization of verotoxin (VT1) into susceptible cells by capping and receptor-mediated endocytosis (RME) (11). Verotoxin is the only glycolipid binding ligand that is internalized into eukaryotic cells by means of RME (12-14). In addition to receptor concentration, both heterogeneous fatty acid composition of $Gb_3$ (15, 16) and phospholipid chain length within the phospholipid bilayer (17) play important roles in binding and internalization of VT. Molecular modeling studies of the $Gb_3$ binding site in the B subunit (18) show that different conformers of membrane $Gb_3$ may bind in different sites. Such conformers may be related to the $Gb_3$ fatty acid content and membrane phospholipid microenvironment (18-20).

The requirement for retrograde transport for intoxication of cells by verotoxin was first demonstrated by Sandvig (21). A431 cells are resistant to VT. These cells expressed $Gb_3$ but the toxin receptor-complex was internalized to endosomes and lysosomes. However, following growth in the presence of butyric acid, an inducer of cell differentiation, A431 cells became VT-sensitive, coincident with the detection of internalized toxin in Golgi cisternae, ER and even in the nuclear envelope (21). Similar targeting of both the holotoxin and B subunit to the nuclear envelope in highly toxin sensitive B lymphomas has been found (11).

In studying the sensitivity of human astrocytoma cell lines to verotoxin, significant differences which do not correlate with the level of receptor expression (6). Similarly, multiple drug resistant (MDR) variants of ovarian tumor cells lines were hypersensitive to VT as compared to the parental cell line, without major increase in receptor expression (22). Based on these discrepancies, $Gb_3$-dependent intracellular traffic plays a major role in determining cell sensitivity to VT.

SUMMARY OF THE INVENTION

The invention relates to hybrid compounds, and methods of preparing and using the same.

In one aspect, the invention provides a hybrid molecule comprising a first domain and a second domain covalently linked, wherein (a) said first domain comprises a domain which is capable of specific binding to $Gb_3$; (b) said second domair comprising a moiety selected from the group consisting of drug moiety, a nucleic acid, a probe, a polypeptide, and a hook, with the proviso that the second domain is not a verotoxin or a fragment thereof. In preferred embodiments, the first domain is a verotoxin or a verotoxin subunit; the first domain is VT-B; the second domain is a polypeptide; the polypeptide is a DNA binding element; the second domain is a nucleic acid; the nucleic acid is an antisense nucleic acid. In another aspect, the invention provides a pharmaceutical composition comprising a hybrid molecule of the invention and a pharmaceutically acceptable carrier.

In another aspect, the invention provides a method for modulating a cell-associated activity comprising contacting a cell with the hybrid molecule of the invention such that a cell associated activity is altered relative to the cell-associated activity of the cell in the absence of the hybrid molecule.

In another aspect, the invention relates to a method for directing the delivery of the hybrid compound of the invention to a particular intracellular location in a cell, the method comprising contacting the cell with the hybrid compound, optionally in the presence of a compound which alters fatty acid composition of $Gb_3$, such that the hybrid compound is delivered to a particular intracellular location in the cell.

In another aspect, the invention provides a use of a hybrid compound of the invention for the manufacture of a medicament for treatment, prophylaxis, or diagnosis.

DETAILED DESCRIPTION OF THE INVENTION

Figure 1:
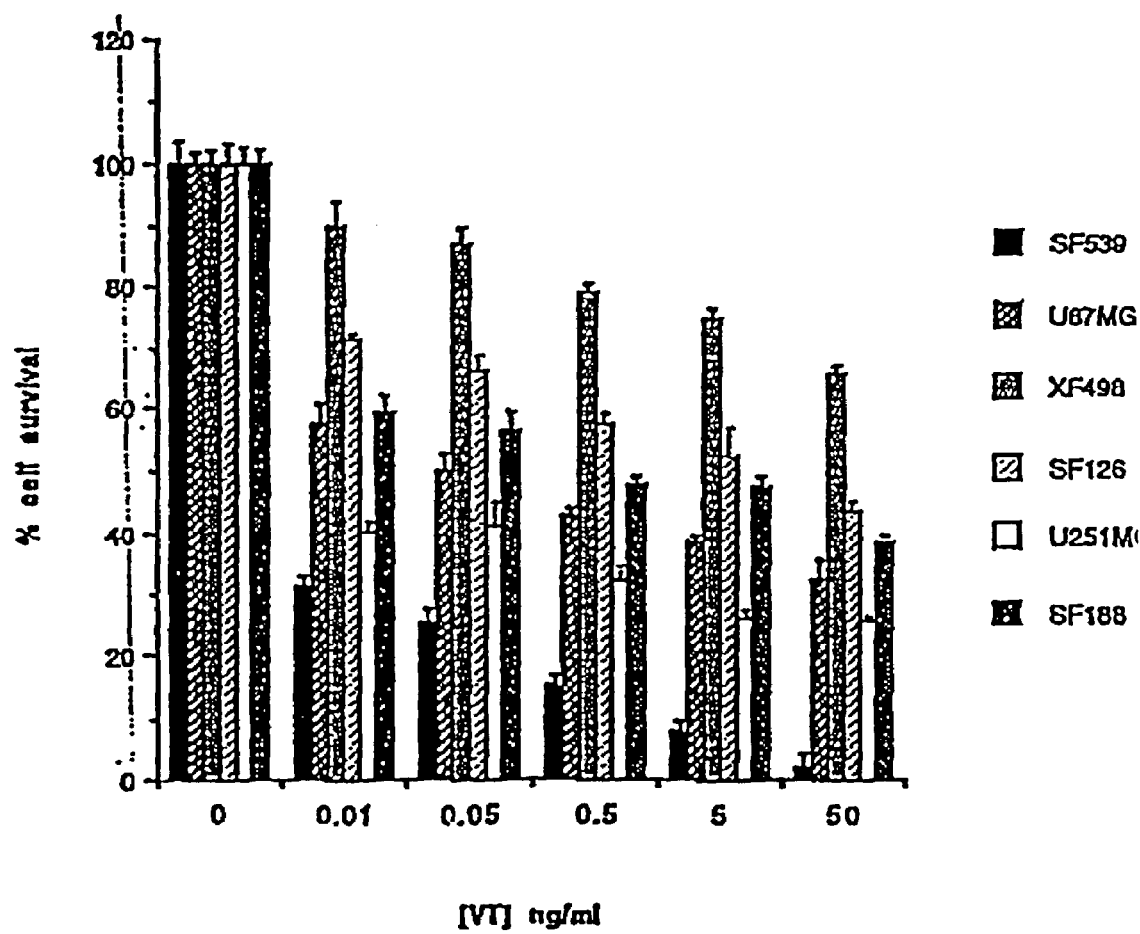
FIG. 1 VT1 cytotoxicity in different human astrocytoma cell lines VT1 cytotoxicity for six astrocytoma cell lines was determined as described in the Methods. SF-539 is the most, and XF-498 is the least sensitive of the cells to VT1 cytotoxicity. Each value represents the mean±S.D. of triplicates. This experiment was repeated three times with similar results.

The invention relates to hybrid compounds, nucleic acids encodingg the hybrid molecules, to methods of preparing the hybrid compounds and nucleic acids which encode them, and to methods of treating subjects with the hybrid compositions.

In one aspect, the invention provides a hybrid compounds. The hybrid compound includes a first domain and a second domain; the first and second domains are, preferably, covalently linked. The first domain is a binding domain capable of specific binding to globotriaosylceramide ($Gb_3$) and being internalized into a cell which expresses $Gb_3$ on the cell surface. The second domain is a functional domain which includes a molecular moiety which is to be delivered into the cell, e.g., to the cell nucleus. The second domain is preferably not a verotoxin, a verotoxin subunit, or a fragment thereof. The second domain can be, for example, a drug moiety (e.g., a drug molecule bound to the first domain), a nucleic acid (e.g., a gene which encodes an exogenous protein, or a nucleic acid which regulates gene expression in a cell, such as antisense nucleic acid, repressors, or trans activators), a probe (such as a fluorescent probe), a protein, and the like. The second domain can also be a domain which functions as a handle or hook for complexation or binding to another moiety or moieties. For example, the second domain can be a member of a specific binding pair (such as biotin/streptavidin, hormone/receptor, binding protein/ligand, and the like), which can be complexed with or bound to the other member of the specific binding pair, which can, in turn, be bound to a moiety which is desired to be delivered into the cell.

A hybrid molecule of the invention can be a fusion protein of the first domain (e.g., verotoxin B subunit (VT-B)) with a proteinaceous second domain (such as a DNA binding protein. The fusion protein can, in certain embodiments, be bound to or complexed with, a moiety to be delivered into a cell. For example, in the example of a VT-B/DNA binding protein fusion (see, e.g., Example 4, infra), the fusion protein can made, optionally purified, and then be bound to a nucleic acid to form a complex of the hybrid compound with the nucleic acid. Upon presentation of the fusion protein/nucleic acid complex to a cell, and endocytosis of the fusion protein, with the associated nucleic acid, into the cell, the nucleic acid is delivered into the cell, for example to the nucleus, e.g., to promote transfection of the cell with the nucleic acid.

A hybrid molecule of the invention can also include a non-fusion covalent adduct of the first domain and the second domain. For examples, methods for covalent modification of proteins are well known, and kits for accomplishing the covalent conjugation of proteins to other protein and non-protein moieties are commercially available. For example, a polypeptide or protein such as VT-B can be linked through the use of heterobifunctional linking agents to moieties such as other proteins, nucleic acids, drugs, probes or labels, and the like. As an example, a first domain, such as VT-B can be covalently linked to a polypeptide such as polylysine (see, e.g., Example 5, infra). Polylysine can complex with nucleic acids such as DNA for delivery of the nucleic acid to a cell (see, e.g., U.S. Pat. Nos. 5,635,383 and 5,166,320 to Wu); thus, a VT-B/polylysine conjugate can be used to bind to a nucleic acid and transport the nucleic acid into a cell, e.g., for applications such as gene therapy, anti-sense therapy, and the like.

In another embodiment, the invention relates to use of a hybrid compound of the invention for in therapy, prophylaxis, or diagnosis, e.g., use of a hybrid compound of the invention for the preparation of a medicament for treatment, prophylaxis, or diagnosis. The hybrid compounds of the invention find use in methods treatments such as treatment of cancer, e.g., by methods such as gene therapy (i.e., by introduction of a gene encoding an exogenous protein into a cell, or introduction of a suppressor or trans activator sequence into a cell), antisense nucleic acid therapy (i.e., by introduction of antisense sequences, e.g., antisense to an oncogene of a cancerous cell); targeting of a chemotherapeutic drug to a cell, and the like.

As described in more detail hereinbelow, the invention further provides methods for altering the intracellular target of a hybrid compound of the invention. Thus, for example, treatment of a cell with sodium butyrate can alter the intracellular destination of VT-B, and therefore a hybrid compound of the invention. As described infra, in certain cells, VT-B is normally transported to components of the Golgi apparatus in the absence of sodium butyrate; however, in the presence of butyrate, VT-B is transported to elements of the endoplasmic reticulum and/or the nuclear envelope. As is also described in more detail hereinbelow, this effect is believed to be due, at least in part, to alterations in the fatty acid composition of the cell surface glycolipid $Gb_3$. The invention contemplates the selective transport of a hybrid compound of the invention to a selected location in the cell, e.g., the nuclear membrane or nucleus. This feature of the invention is especially useful for gene therapy applications (or antisense treatments) in which the nuclear genome, rather than the DNA in the cytoplasm or cytoplasmic organelles, is to be targeted. Accordingly, in certain embodiments, the invention contemplates treatment of a cell with a compound (e.g., butyrate), or under conditions, capable of effecting a change in the fatty acid composition of Gb3, and thereby promoting selective transport of a hybrid compound of the invention to a pre-selected intracellular location (e.g., the nucleus).

It will be appreciated by the skilled artisan that use of the hybrid compounds of the invention provides benefits such as specificity of cell targeting, the ability to deliver almost any therapeutic moiety to a cell, the ability to specifically target subcellular structures, and the like. For example, it is well known that certain cell types, including certain cancer cells, express large amounts of $Gb_3$ on the cell surface, while other cell types express little $Gb_3$ at the cell surface. The hybrid compounds of the invention will be readily endocytosed by the former cell types, but will be less readily transported into the latter cell type. Thus, a cell type which express large amounts of $Gb_3$ on the cell surface can be selectively targeted using the hybrid compounds of the invention. Importantly, certain cancer cells show greater $Gb_3$ levels than normal cells; for example, primary ovarian tumor cells have been found to show greater levels of $Gb_3$ than normal ovarian tissue cells. Thus, the hybrid compounds of the invention can be used to deliver a drug, a gene, or another therapeutic agent specifically to cancerous cell types while sparing normal tissues.

The First Domain The first domain of the hybrid compounds of the invention comprises a domain which is capable of specific binding to globotriaosylceramide ($Gb_3$), and is capable of being internalized into a cell which expresses $Gb_3$ on the cell surface; such a domain will for convenience sometimes be referred to herein as a "VT binding domain" although, as described herein, first domains suitable for use in the invention are not limited to verotoxins or fragments thereof. Domains suitable for use as a first domain of a hybrid compound of the invention include native verotoxins (VTs), subunits of verotoxins (e.g., VT-B subunit) which bind to $Gb_3$, and polypeptides comprising amino acid sequences homologous to and/or derived from the amino acid sequence of a native VT binding domain, which can include more, fewer (e.g., a deletion or truncation), or an equal number (e.g., point mutations) of amino acids than a full length VT binding domain protein, while retaining substantial specific binding affinity for $Gb_3$ (or Burkitt's lymphoma associated antigen (BLA) (Nudelman, et al. *Science* 220:509 (1983), also known as the B-cell differentiation antigen CD77). Thus, a "VT binding domain", as used herein, refers to the $Gb_3$ receptor binding subunit of verotoxins or homologous domains which have $Gb_3$ binding activity. It will be appreciated that certain proteins or polypeptides are known which have substantial homology to verotoxin binding domains (e.g., CD19, a 95 kDa immunoglobulin superfamily integral membrane glycoprotein present on the cell surface of human B lymphocytes from the early stage of B-cell development to the terminal differentiation of B-cells to plasma cells (Nadler, et al. *J. Immunol.* 131:244-250 (1983); Lingwood, C. A. (1996) *Trends in Microbiol.* 4(4):147-153; Maloney, M. D. and Lingwood, C. A. (1994) *J. Exp. Med.* 180:191-201; Nyholm, P. G., Magnusson, G. and Lingwood, C. (1996) *Chem. Biol.* 3:263-275) and can bind to $Gb_3$ or Gb3-like cell surface moieties; use of such homologous proteins or polypeptides is contemplated in the hybrid compounds of the invention. In one embodiment, the first domain of a hybrid compound of the invention is at least about 30%, 40%, more preferably at least about 50%, 60%, even more preferably at least about 70%, 80%, yet even more preferably at least about 90%, and most preferably at least about 95% (or more) homologous to a $Gb_3$ binding domain of a native verotoxin (or verotoxin subunit). Typically, biologically active portions comprise a domain or motif with at least one activity of a VT binding domain. A biologically active portion of a VT binding domain protein can be a polypeptide which is, for example, 10, 25, 50, 100 or more amino acids in length.

In one embodiment, a biologically active portion of a VT binding domain protein comprises at least one $Gb_3$ binding domain. In other embodiments, a biologically active portion of a VT binding domain protein comprises two, three or four $Gb_3$ binding domains.

Moreover, other biologically active portions, in which other regions of the protein are deleted, can be prepared by recombinant techniques and evaluated for one or more of the functional activities of a native VT binding domain protein. It will be appreciated by the skilled artisan that VT holotoxin has significant toxicity to certain cell types. The toxicity of VT holotoxin is largely (although not entirely) due to the A subunit of VT; isolated VT-B has much lower toxicity to most cell types than does the holotoxin. Accordingly, in preferred embodiments, a hybrid compound of the invention does not comprise VT subunit, or portion thereof, which confers cell toxicity on VT holotoxin; e.g., in preferred embodiments, a hybrid compound of the invention does not include VT A subunit, or any substantially cytotoxic portion thereof. Thus, in a preferred embodiment, the first domain of a hybrid compound of the invention consists essentially of VT-B, or a homolog thereof, or a fragment thereof, which is substantially free of VT A subunit or portions of VT A subunit. Of course, if it desired to use a hybrid compound of the invention to kill a cell (such as a cancer cell or a virally-infected cell), a toxic moiety can be employed as the second domain, e.g., all or part of a toxic protein such as ricin, diphtheria toxin, tetanus toxin, and the like.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

The Second Domain

The second domain of a hybrid compound of the invention can be almost any moiety which is desired to be transported into a cell (either in vitro or in vivo) and which is capable of being bound (e.g., through a covalent bond) to the first domain of the compound of the invention. The second domain also can be a handle or hook for binding or complexing to a third component (e.g., a nucleic acid, and the like).

Examples of second domains contemplated for use in the hybrid compounds of the invention include proteins, polypeptides, and fragments thereof (including peptidomimetics, amino acid analogs, and the like). For example, a second domain can comprise a protein (e.g., erythropoeitin, human growth hormone, insulin, somatostatin, EGF, and Interleukins I, II,III, IV and VI, and the like. It will be appreciated that the use of a second domain which itself has a particular specificaty for a cell surface receptor can provide additional specificity to the hybrid compound of the invention when administered to a subject, e.g., a human or animal. For example, a hybrid compound which include VT-B as a first domain and substance P as a second domain may preferentially target cells which express both $Gb_3$ and substance P receptors.

Additional examples of second domains include nucleic acids, e.g., DNA, RNA, DNA/RNA chimeric nucleic acids, and the like, as well as analogs of nucleic acids such as phosphorothioate nucleic acids (see, e.g., Cornish et al., *Pharmacol. Com.* 3:239-247, 1993; Crooke, *Ann. Rev. Pharm. Toxicol.* 32:329-376, 1992; Iversen, *Anti-Cancer Drug Design* 6:531-538, 1991). A nucleic acid can, e.g., encode a protein or fragment thereof, can be a regulatory sequence such as a repressor or promoter sequence, or can be a complement to a nucleotide sequence present in a cell, e.g., for use in antisense therapy.

Still further examples of second domains useful in the hybrid compounds of the invention include hormones (e.g., steroids) or other biologically active moieties (e.g., retinoids).

Yet further examples of second domains include probes, e.g., probes for examining cell structure (e.g., for use in vitro, including radioisotope labels, fluorescent labels, heavy atom labels such as gold particles, and the like), labels for in vivo studies (e.g., labels detectable by X-ray, magnetic resonance imaging, and the like). Thus, the invention provides hybrid compounds which find use as diagnostic agents, e.g., for use in cell culture studies or when formulated in a pharmaceutically acceptable vehicle for administration to a subject.

Still other examples of second domains include a handle or hook for binding or complexing to a third component. For example, a second moiety can be a member of a specific binding pair (e.g., receptor/ligand, hormone/receptor, nucleic acid/complement, enzyme/ligand, and the like). A hybrid compound which includes a hook as a second domain can then be used to transport a complementary molecule into a cell by endocytosis, e.g., a hybrid compound which includes a streptavidin sequence (or portion thereof) can be used to bind to biotin, which in turn can be bound or coupled to a moiety for delivery into a cell (e.g., a biotinylated nucleic acid, or the like). A second moiety can also be, e.g., a moiety which binds non-specifically to a third component which is to be delivered to a cell. For example, a VT-B/polycation (e.g., polylysine) hybrid compound (see, e.g., Example 5, infra) can be used to deliver a negatively-charged compound (e.g., a nucleic acid such as DNA) to a cell for endocytosis.

Hybrid Compounds

The invention thus contemplates a wide variety of hybrid compounds, which have a great number of uses.

In certain embodiments, the hybrid compounds of the invention include a first domain and a second domain (e.g., as described above), covalently linked. The covalent linkage can be provided in many ways, which will be routine to the ordinarily skilled artisan. For example, the second domain can be covalently bound to the first domain through chemistry known for the covalent modification of proteins, e.g., the use of heterobifunctional linkers, in which one functional group can react with a functional group of a protein (e.g., the first domain) (e.g., a side chain thiol, amine, or carboxylate of the first domain) and a second functional group which can react with a moiety of the second domain (e.g., a side chain group where the second domain is a polypeptide, a hydroxyl group of a nucleic acid, a drug, or a hormone, and the like). A wide variety of bifunctional or polyfunctional cross-linking reagents, both homo- and heterofunctional, are known in the art and are commercially available (e.g., Pierce Chemical Co., Rockford, Ill.). accordingly, one of ordinary skill in the art will be able to prepare a wide variety of hybrid compounds of the invention using no more than routine experimentation.

The invention also provides fusion proteins, e.g., VT binding domain chimeric or fusion proteins. The term "fusion protein" is intended to describe at least two polypeptides, typically from different sources, which are operatively linked. With regard to the polypeptides, the term "operatively linked" is intended to mean that the two polypeptides are connected in manner such that each polypeptide can serve its intended function. Typically (although not exclusively), the two polypeptides are covalently attached through peptide bonds. The fusion protein is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

Thus, a VT binding domain "chimeric protein" or "fusion protein" comprises a first domain, e.g., a VT binding domain polypeptide operatively linked to a second domain, e.g., a second polypeptide, which preferably is a non-VT binding domain polypeptide, e.g., a polypeptide which is not substantially homologous to a VT binding domain protein, e.g., a protein which is different from the VT binding domain protein and which is derived from the same or a different organism. The second domain polypeptide can be fused to the N-terminus or C-terminus of the first domain polypeptide. In a preferred embodiment, the second domain comprises at least about 5 amino acid residues, more preferably about 10, 20, 30, 40, 50, 100 or 200 amino acid residues.

For example, in one embodiment a VT binding domain fusion protein comprises a $Gb_3$ binding domain operably linked to the extracellular domain of a second protein. Such fusion proteins can be further utilized in delivering molecules to the intracellular region of a cell, e.g., delivery of pharmaceutical compositions.

In yet another embodiment, the fusion protein is a GST-VT binding domain fusion protein in which the VT binding domain sequences are fused to the C-terminus of the GST sequences. Such fusion proteins can facilitate the purification of recombinant VT binding domain.

Preferably, a VT binding domain chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhargs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A VT binding domain-encoding nucleic acid can be cloned into such an expression vector such that the fusion moiety is linked in-frame to the VT binding domain protein.

It will be appreciated from the foregoing that the invention also provides nucleic acids (e.g., DNA) which encode the fusion proteins of the invention. Nucleic acids which encode the fusion proteins of the invention are nucleic acids of the invention.

In one embodiment, variants of the VT binding domain portion of the VT binding domain fusion protein which function as either VT binding domain agonists (mimetics) or as VT binding domain antagonists can be identified by screening combinatorial libraries of mutants, e.g., truncation mutants, of the VT binding domain protein for VT binding domain protein agonist or antagonist activity. In one embodiment, a variegated library of VT binding domain variants is generated by combinatorial mutagenesis at the nucleic acid level and is encoded by a variegated gene library. A variegated library of VT binding domain variants can be produced by, for example, enzymatically ligating a mixture of synthetic oligonucleotides into gene sequences such that a degenerate set of potential VT binding domain sequences is expressible as individual polypeptides, or alternatively, as a set of larger fusion proteins (e.g., for phage display) containing the set of VT binding domain sequences therein. There are a variety of methods which can be used to produce libraries of potential VT binding domain variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential VT binding domain sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the VT binding domain protein coding sequence can be used to generate a variegated population of VT binding domain fragments for screening and subsequent selection of variants of a VT binding domain protein. In one embodiment, a library of coding sequence fragments can be generated by treating a double stranded PCR fragment of a VT binding domain coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the VT binding domain protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of VT binding domain proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify VT binding domain variants (Arkin and Yourvan (1992) *PNAS* 89:7811-7815; Delgrave et al. (1993) *Protein Engineering* 6(3):327-331).

An isolated VT binding domain protein, or a portion or fragment thereof, can be used as an immunogen to generate antibodies that bind VT binding domain using standard techniques for polyclonal and monoclonal antibody preparation. The full-length VT binding domain protein can be used or, alternatively, the invention provides antigenic peptide fragments of VT binding domain for use as immunogens. The antigenic peptide of VT binding domain comprises at least 8 amino acid residues of the amino acid sequence of VT binding domain such that an antibody raised against the peptide forms a specific immune complex with VT binding domain. Preferably, the antigenic peptide comprises at least 10 amino acid residues, more preferably at least 15 amino acid residues, even more preferably at least 20 amino acid residues, and most preferably at least 30 amino acid residues.

An antibody according to the invention can be used to deliver a moiety into a cell, e.g., a moiety can be bound to an antibody, and the antibody can be bound to a VT binding domain. The complex can then be internalized into a cell as described herein, thereby delivering the moiety to the cell.

A VT binding domain immunogen typically is used to prepare antibodies by immunizing a suitable subject, (e.g., rabbit, goat, mouse or other mammal) with the immunogen. An appropriate immunogenic preparation can contain, for example, recombinantly expressed VT binding domain protein or a chemically synthesized VT binding domain polypeptide. The preparation can further include an adjuvant, such as Freund's complete or incomplete adjuvant, or similar immunostimulatory agent. Immunization of a suitable subject with an immunogenic VT binding domain preparation induces a polyclonal anti-VT binding domain antibody response.

Accordingly, another aspect of the invention pertains to anti-VT binding domain antibodies. The term "antibody" as used herein refers to immunoglobulin molecules and immunologically active portions of immunoglobulin molecules, i.e., molecules that contain an antigen binding site which specifically binds (immunoreacts with) an antigen, such as VT binding domain. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind VT binding domain. The term "monoclonal antibody" or "monoclonal antibody composition", as used herein, refers to a population of antibody molecules that contain only one species of an antigen binding site capable of immunoreacting with a particular epitope of VT binding domain. A monoclonal antibody composition thus typically displays a single binding affinity for a particular VT binding domain protein with which it immunoreacts.

Polyclonal anti-VT binding domain antibodies can be prepared as described above by immunizing a suitable subject with a VT binding domain immunogen. The anti-VT binding domain antibody titer in the immunized subject can be monitored over time by standard techniques, such as with an enzyme linked immunosorbent assay (ELISA) using immobilized VT binding domain. If desired, the antibody molecules directed against VT binding domain can be isolated from the mammal (e.g., from the blood) and further purified by well known techniques, such as protein A chromatography to obtain the IgG fraction. At an appropriate time after immunization, e.g., when the anti-VT binding domain antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *PNAS* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer*

*Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a VT binding domain immunogen as described above, and the culture supernatants of the resulting hybridoma cells are screened to identify a hybridoma producing a monoclonal antibody that binds VT binding domain.

Any of the many well known protocols used for fusing lymphocytes and immortalized cell lines can be applied for the purpose of generating an anti-VT binding domain monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-4, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind VT binding domain, e.g., using a standard ELISA assay.

Alternative to preparing monoclonal antibody-secreting hybridomas, a monoclonal anti-VT binding domain antibody can be identified and isolated by screening a recombinant combinatorial immunoglobulin library (e.g., an antibody phage display library) with VT binding domain to thereby isolate immunoglobulin library members that bind VT binding domain. Kits for generating, and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc. Acid Res.* 19:4133-4137; Barbas et al. (1991) *PNAS* 88:7978-7982; and McCafferty et al. *Nature* (1990) 348:552-554.

Additionally, recombinant anti-VT binding domain antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *PNAS* 84:3439-3443; Liu et al. (1987) *J. Immunol.* 139:3521-3526; Sun et al. (1987) *PNAS* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-VT binding domain antibody (e.g., monoclonal antibody) can be used to isolate VT binding domain by standard techniques, such as affinity chromatography or immunoprecipitation. An anti-VT binding domain antibody can facilitate the purification of natural VT binding domain from cells and of recombinantly produced VT binding domain expressed in host cells. Moreover, an anti-VT binding domain antibody can be used to detect VT binding domain protein (e.g., in a cellular lysate or cell supernatant) in order to evaluate the abundance and pattern of expression of the VT binding domain protein. Anti-VT binding domain antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Recombinant Expression Vectors and Host Cells

Another aspect of the invention pertains to vectors, preferably expression vectors, containing a nucleic acid encoding a fusion protein of the invention, e.g., a nucleic acid sequence encoding a VT binding domain (or a portion thereof) operatively linked to at least one other nucleic acid sequence which encodes a polypeptide (e.g., a second domain of a hybrid compound of the invention), in a form suitable for expression of the fusion protein in a host cell. The term "in a form suitable for expression of the fusion protein in a host cell" is intended to mean that the recombinant expression vector includes one or more regulatory sequences operatively linked to the nucleic acid encoding the fusion protein in a manner which allows for transcription of the nucleic acid into mRNA and translation of the mRNA into the fusion protein. The term "regulatory sequence" is art-recognized and intended to include promoters, enhancers and other expression control elements (e.g., polyadenylation signals). Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the amount of fusion protein to be expressed.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. For example, replication defective retroviruses, adenoviruses and adeno-associated viruses can be used. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. The genome of adenovirus can be manipulated such that it encodes and expresses a transactivator fusion protein but is inactivated in terms of its ability to replicate in a normal lytic viral life cycle. See for example Berkner et al. (1988) *BioTechniques* 6:616; Rosenfeld et al. (1991) *Science* 252: 431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are well known to those skilled in the art. Alternatively, an adeno-associated virus vector such as that described in Tratschin et al. (1985) *Mol. Cell. Biol.* 5:3251-3260 can be used to express a fusion protein of the invention.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., VT binding domain proteins, mutant forms of VT binding domain, fusion proteins, etc.).

The recombinant expression vectors of the invention can be designed for expression of VT binding domain operatively linked to other molecules in prokaryotic or eukaryotic cells. For example, VT binding domain operatively linked to another molecule can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promotors directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5

(Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the Fusion protein expression vector is a yeast expression vector. Examples of vectors for expression in yeast *S. cerivisae* include pYepSec1 (Baldari, et al., (1987) *Embo J.* 6:229-234), pMFa (Kurjan and Herskowitz, (1982) *Cell* 30:933-943), pJRY88 (Schultzet al., (1987) *Gene* 54:113-123), pYES2 (Invitrogen Corporation, San Diego, Calif.), and picZ (InVitrogen Corp, San Diego, Calif.).

Alternatively, VT binding domain operatively linked to other molecules can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *PNAS* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the a-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to VT binding domain mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a fusion protein of the invention can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding A fusion protein of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) VT binding domain protein operatively linked to other molecules. Accordingly, the invention further provides methods for producing VT binding domain protein operatively linked to other molecules using the host cells of the invention. In one embodiment, the method comprises culturing the host cell of invention (into which a recombinant expression vector encoding VT binding domain operatively linked to other molecules has been introduced) in a suitable medium such that VT binding domain protein operatively linked to other molecules is produced. In another embodiment, the method further comprises isolating VT binding domain operatively linked to other molecules from the medium or the host cell.

The host cells of the invention can also be used to produce nonhuman transgenic animals. For example, in one embodiment, a host cell of the invention is a fertilized oocyte or an embryonic stem cell into which VT binding domain-coding sequences operatively linked to other coding sequences have been introduced. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal.

A transgenic animal of the invention can be created by introducing VT binding domain-encoding nucleic acid operatively linked to another nucleic acid molecule into the male pronuclei of a fertilized oocyte, e.g., by microinjection, retroviral infection, and allowing the oocyte to develop in a pseudopregnant female foster animal. A tissue-specific regulatory sequence(s) can be operably linked to the VT binding domain transgene to direct expression of VT binding domain hybrid protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the A fusion protein of the invention transgene in its genome and/or expression of A fusion protein of the invention mRNA in tissues or cells of the animals. A transgenic founder animal can then be used to breed additional animals carrying the transgene. Moreover, transgenic animals carrying a transgene encoding A fusion protein of the invention can further be bred to other transgenic animals carrying other transgenes.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The nucleic acid molecules of the invention (e.g., nucleic acids which encode a fusion protein of the invention), hybrid compounds of the invention, and anti-VT binding domain antibodies (also referred to herein as "active compounds") of the invention can be incorporated into pharmaceutical compositions suitable for administration. Such compositions typically comprise the nucleic acid molecule, hybrid compound, or antibody, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a hybrid compound o the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors, e.g., as described hereinabove. Gene therapy vectors can be delivered to a subject by, for example, intravenous injection, local administration (see U.S. Pat. No. 5,328,470) or by stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

Uses and Methods of the Invention

The nucleic acid molecules, hybrid compounds, and antibodies described herein can be used for methods of treatment. As described herein, a hybrid compound of the invention can have the following activities: (i) it can interact with (e.g., bind to) specific receptors on the surface of a cell, e.g., $Gb_3$; (ii) while bound to its receptor, it is internalized into the cell; and (iii) it is delivered to a specific location within the cell. Thus, a VT-binding domain bound (e.g., through a covalent bond) to another moiety can be used to (i) internalize small molecules, e.g., peptides, nucleic acid molecules; (ii) internalize pharmaceutical compositions; and (iii) specifically target intracellular locations.

Thus, in a broad aspect, the invention relates to methods for modulating a cell-associated activity (e.g., cell growth, replication, expression of an endogenous or exogenous gene product, and the like). An exemplary method includes contacting a cell with a hybrid compound of the invention, such that a cell associated activity is altered relative to the cell-associated activity of the cell in the absence of the hybrid compound.

The invention also relates to methods for targeting a moiety for internalization into a $Gb_3$-containing cell. The method includes the step of contacting the cell with a hybrid compound of the invention, wherein the hybrid compound includes the moiety for internalization, such that the hybrid compound is internalized into the cell. The moiety can be any moiety which is to be delivered into the cell, e.g., a toxin (e.g., for killing the cell), a polynucleotide, e.g., a gene, (e.g., for genetic modification, e.g., for expression of a gene product in the cell), a protein or peptide (e.g., an antibody or antigen), and the like. The $Gb_3$-binding moiety can be, e.g., an anti-$Gb_3$ antibody, as described supra. The targeted moiety can be bound or conjugated to the $Gb_3$-binding moiety as described above.

Accordingly, the invention relates to methods for treatment, prophylaxis, or diagnosis of a subject, e.g., an animal, including a mammal (including both non-human animals and humans). In one embodiment, the invention provides use of a hybrid compound for treatment, therapy or diagnosis of a subject. In one embodiment, the invention provides use of a hybrid compound of the invention for the manufacture of a medicament for the treatment, diagnosis or prophylaxis in a subject. In one embodiment, a method comprises administering to a subject a hybrid compound of the invention, such that a disease state is treated. For example, in one embodiment, the hybrid compound comprises a first domain comprising VT-B, and a second domian, covalently bound to the first domain, comprising a nucleic acid which encodes a gene. Administration of the hybrid compound (optionally in a pharmaceutically acceptable carrier) provides a means for delivering the gene to cells which express $Gb_3$. The cell can then be integrated into the cellular genome and the gene product can be expressed by the cell. For example, the gene could encode the enzyme adenosine deaminase (ADA), an enzyme which is absent in subjects suffering from ADA deficiency, e.g., as a result of an inborn genetic deficiency. The invention thus relates to methods for the treatment of genetic defects, e.g., by gene therapy. In another embodiment, the hybrid compound comprises a first domain comprising VT-B, and a second domian, covalently bound to the first domain, comprising an enzyme., e.g., an enzyme which is absent (or present in insufficient amount) in a subject, or in a tissue of a subject. For example, the enzyme could be, e.g., ADA.

This invention is further illustrated by the following examples which should not be construed as limiting. The contents of all references, patent applications, patents, and published patent applications cited throughout this application are hereby incorporated by reference.

EXAMPLES

The following materials and methods were used in the Examples:

Verotoxin Purification

Recombinant VT binding domain1 from pJLB28 (23), and VT binding domain1 B subunit (24) were purified by a recently developed affinity chromatographic technique (25), aliquoted in PBS and stored at −70° C. Purified B subunit was labeled with fluorescein (or rhodamine) isothiocyanate as described (11).

Cell Culture

Permanent human malignant astrocytoma cell lines (SF-126, SF-188, SF-539, U 87-MG, U 251-MG, and XF-498 (provided by Dr. J Rutka) HSC (26-29). All cell lines were grown in monolayers in a-MEM (GIBCO) plus nonessential amino acids, glutamine, gentamycin, and 10% heat-inactivated fetal bovine serum, except XF-498 (which was grown in RPMI media) and SKVLB (grown in the presence of 1 μg/ml vinblastine) which is multi-drug resistant variant of the parental SKOV3 ovarian carcinoma cell line (30).

Verotoxin Cytotoxicity

Semiconfluent cells in microtiter plates were incubated in triplicates with ten fold VT binding domain dilutions and remaining cells after 72 hr were quantitated by staining with 0.1% crystal violet and measuring the optical density at 570 nm using a microtiter plate reader (31).

FIG. 1 shows the cytotoxic response of six astrocytoma cell lines to increasing concentrations of VT binding domain1. Although each cell line was sensitive to VT binding domain1, a >5000 fold difference in sensitivity between the most (SF-539) and least (XF-498) sensitive cell line was apparent.

We previously showed that the multiple drug resistant ovarian carinoma variant cell lines SKVLB and SKOVC were ~1000 fold more sensitive to VT binding domain compared to the parental SKOV3 cell line (22).

Glycolipid Extract of Cultured Cells

After trypsinization, cells (~1×10$^6$) were washed with PBS three times, resuspended in a minimum volume, and extracted with 20 volumes of chloroform/methanol (C/M) 2:1 by vol. The extract was partitioned against water and the lower phase partitioned again against theoretical upper phase. The combined lower phase was then evaporated, saponified with 1 N NaOH in methanol and glycolipids reextracted as above. The dried lower phase was dissolved in CM 98:2 and separated by silica chromatography (32). The column was washed extensively with chloroform and glycolipid eluted in acetone/methanol (9:1 by vol.). Gb3 present was detected by tlc overlay binding with VT binding domain1 (16).

Assay of $Gb_3$ Content by VT Binding Domain1 TLC Overlay

Aliquots of the glycolipid extract of human tumor samples or of tumor cell lines were separated by TLC {chloroform, methanol, water-65:25:4 (v/v/v)}. The plates were dried and blocked with 1% gelatin in water at 37° C. overnight. They were then washed three times with 50 mM TBS for 5 min and incubated with 0.1 µg/ml toxin for 1 hour at R.T. After further washing with TBS, plates were incubated with mouse monoclonal anti-VT binding domain1 antibody (33) (2 µg/ml) for VT binding domain1 followed by peroxidase-conjugated goat anti-mouse antibody. Finally, the plates were washed with TBS, and toxin binding was visualized with 4-chloro-1-naphthol peroxidase substrate. A similar plate was prepared and sprayed with orcinol for comparison of glycolipid content.

Since the presence of the toxin receptor glycolipid, $Gb_3$ is essential to confer sensitivity to VT binding domain, the $Gb_3$ content of the six astrocytoma cell lines analyzed by tlc overlay. Each of the astrocytoma cell lines expressed significant levels of $Gb_3$. SF-539, the most, and XF-498, the least sensitive cell lines, expressed the highest receptor level. Thus $Gb_3$ content is not sufficient to explain the marked difference in sensitivity to VT binding domain of these cells.

Previous VT binding domain1 tlc overlay analysis of $Gb_3$ content was also suggestive of increased levels of a slower migrating $Gb_3$ species in SKVLB (22). Comparative HPLC analysis of the fatty acid methyl esters of $SKOV_3$ and SKVLB $Gb_3$ was performed (table 1). As for the astrocytoma cells, no fatty acids shorter than C12 and no hydroxy fatty acids were detected. The results show a marked elevation in short chain fatty acids in SKVLB as compared to $SKOV_3$ $Gb_3$, -C16:0 and particularly C18:0 fatty acids, whereas the content of long chain fatty acids, C22:0, 24:0, and 24:1, is greatly reduced in comparison to SKOV3 $Gb_3$. Thus the change in $Gb_3$ fatty acid content for the MDR cell line SKVLB, is similar to the difference observed for SF 529 vs XF 498 cells and the change found following butyrate treatment of XF 498 cells. In each case, increased sensitivity to VT binding domain1 correlated with an increased proportion of short chain fatty acid $Gb_3$ species.

Cell Sensitization to VT Binding Domain by Butyrate Treatment

XF-498 astrocytoma, ovarian tumour and vero cell lines were cultured in media containing 2 mM sodium butyrate (or propionate or capronate for astrocytoma cells).

Sodium butyrate has been found to increase sensitivity to VT binding domain in several cell systems (12, 13, 43, 44). We therefore determined the effect of butyrate on the VT binding domain sensitivity of XF-498 cells.

morphology and growth: Initial studies showed butyrate treatment of XF-498 cells had a profound effect on the morphology of these cells. XF-498 cells are small, round cells that pile up, and even upon confluency, do not form a monolayer. In contrast, SF-539 cells are flat, stellate and form a confluent monolayer. Butyrate treated XF-498 cells adopt a similar morphology to SF-539 cells. XF498 cells cultured in propionate showed a similar, but less significant, morphological change but culture of XF498 cells in capronate had no effect. PPMP inhibition of glycolipid biosynthesis (45) prevented the butyrate-induced morphological changes. PPMP alone had no effect on XF 498 morphology.

VT binding domain1 sensitivity: In addition to effecting a morphological change to more resemble SF596 cells, butyrate induced a significant (5000 fold) increase in XF-498 cell sensitivity to VT binding domain1. VT binding domain1 sensitivity was increased to a lesser extent for propionate treated cells, but capronate had no effect. PPMP prevented butyrate induced VT binding domain1 sensitivity of XF-498 cells (not shown) as Sandvig has reported (46).

subcellular VT binding domain targeting: Concommittant with the increased sensitivity to VT binding domain1 induced by butyrate treatment of XF 498 cells, butyrate induced a marked change in the intracellular routing of VT binding domain1 B, such that the toxin became localized mainly around the ER/nuclear membrane as for SF-539. Serial sectioning shows the B subunit to be, in part, located within a restricted region of the nucleus. Pixel integration of "z" scans across the nucleus in the composite confocal images shows three labeling maxima corresponding to the nuclear boundaries and a central intranuclear peak in SF 529 cells but a single juxtanuclear peak in XF 498 cells without peri- or intranuclear staining. After butyrate treatment, the major labeling for XF 498 cells is within the nucleus.

Immunoelectron microscopy further confirmed the nuclear location of VT binding domain1 B in SF-539 and butyrate treated XF-498 cells. In untreated XF 498 cells, VT binding domain1B was detected in the Golgi but nuclear labeling was not above background.

$Gb_3$ expression: Butyrate treatment has been previously found to induce $Gb_3$ synthesis to mediate increased VT binding domain sensitivity (43, 46). The $Gb_3$ content of SF 539 cell was therefore compared to that of XF 498 cells before and after butyrate treatment by VT binding domain1-tlc overlay. It can be seen that the $Gb_3$ contained within XF 498 cells runs on tlc as single band corresponding to the faster $Gb_3$ band of the renal standard. In contrast, SF 539 cells contain an additional slower migrating $Gb_3$ band. Following butyrate treatment, there is a dramatic, selective increase in this slower $Gb_3$ band in XF 498 cells, such that this band now becomes the dominant VT binding domain1 binding $Gb_3$ species. This $Gb_3$ species is also selectively increased, but to a lesser extent, following propionate treatment, whereas capronate has no effect.

$Gb_3$ fatty acid isoform expression: HPLC analysis of the fatty acid composition of the $Gb_3$ purified from SF 539 and XF 498 cells before and after butyrate treatment showed that the SF 539 $Gb_3$ species was enriched in short chain fatty acids (C16 and C18) and deficient in the longer chain species (C22, C24) relative to XF 498 $Gb_3$. Sub fractionation of the $Gb_3$ species in butyrate treated XF 498 into slow, 'intermediate' and fast fractions confirmed the markedly increased C16 and decreased C24 fatty acid content of the slow migrating $Gb_3$ species induced by butyrate.

Figure 2:
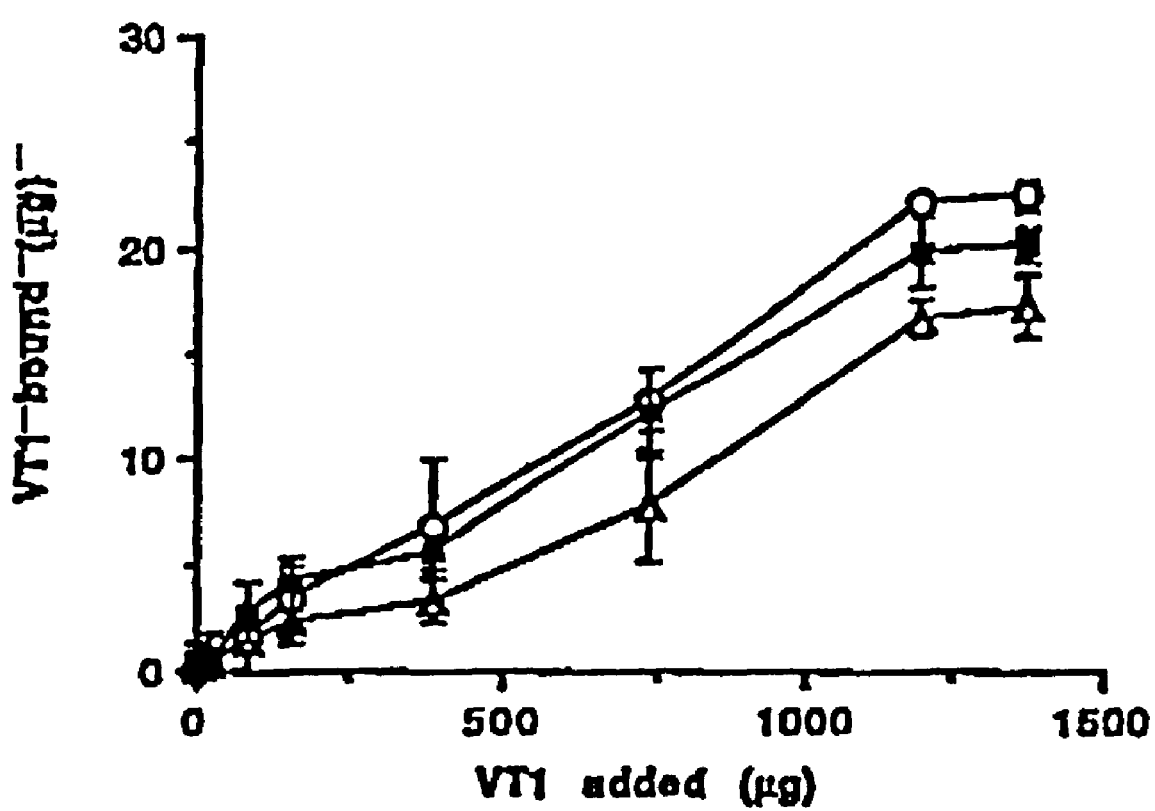
FIG. 2 Astrocytoma cell surface $^{125}$I VT1 binding SF 539 (■), XF 498 (○) and butyrate treated XF 498 (Δ) cells were treated with serial dilutions of $^{125}$I-VT1 in PBS at 4° C., incubated for 1 h and binding was determined as described in the Methods. All three cell lines demonstrate similar level of VT1 binding. Each value represents the mean±S.D. of triplicate determinations.

Cell surface VT binding domain1 binding: To preclude the differential VT binding domain1 sensitivity of astrocytoma cells being due to differences in toxin binding, cell surface binding at 4° C. was quantitated using $^{125}$I-labeled VT binding domain1. The comparison of XF498 (with and without butyrate treatment) and SF 539 is shown in FIG. 2. All three cell 'types' demonstrate comparable VT binding domain1 binding. If anything, the more VT binding domain susceptible butyrate treated cells show less VT binding domain binding.

Electron Microscopy

Targeting of VT binding domain1 in SF-539 and XF-498 cells was examined in detail by transmission EM. Cells were cultured on a transferable membrane inserts in 24 well tissue culture plates and allowed to form a confluent monolayer. For surface binding, the cells were incubated at 4° C. in the presence of 5 µg/ml VT1B for 30 min and washed with cold PBS. Then, cells were incubated with anti-VT1B primary antibody followed by GAM-gold secondary antibody for 30 min at 4° C. For toxin internalization studies, cells were incubated with VT 1 B (5 µg/ml) at 37° C. for 1 hr. For either treatment, the cells were fixed in 2.5% gluteraldehyde, 2% paraformaldehyde in PBS for 30 min at room temperature. After washing with PBS, cells were post fixed in 1% osmium tetroxide in phosphate buffer for 30 min and washed with saline. The cells were further postfixed with 2% uranyl acetate in 30% ethanol for 15 min (38), and dehydrated in an ethanol gradient. Dehydrated cells were serially infiltrated with 50% to 75% Epon in 100% ethanol for 30 min each and finally with 100% Epon for 1 h with 2 changes of Epon. The membrane was removed from the holder and inserted vertically into the gelatin capsule, filled with 100% Epon and polymerized at 65° C.

After sectioning of the polymerized block on an ultramicrotome, the sections for surface binding studies were counter stained, while the sections for studies of internalization were immunolabeled. These sections were treated with saturated sodium metaperiodate for 30 min to unmask antigenicity (39) and washed in distilled water. The sections were next blocked by floating on a drop of 0.1% BSA, 0.2% fish skin gelatin in 50 mM TBS (150 mM NaCl, 50 mM Tris, pH 7.4) for 30 min and immunolabeled with 1:50 dilution of anti-VT binding domain1B antibody, followed by 1:50 dilution of GAM-15 or -10 nm gold for 1 h each at room temperature, with through washing after each step. Finally, the sections were stained with 5% uranyl acetate and then with Reynold's lead citrate for 6 min each and analyzed under a Philips 300 EM microscope at 60 kV.

Example 1

Preparation of a Labeled Hybrid VT Binding Domain Moiety

Lysosomal Labeling (FITC-Dextran and RITC-VT Binding Domain1B Double Labeling)

Internalization of FITC-dextran was used as a lysosomal marker as previously (34). Cells grown overnight on cover slips were incubated with 0.5 µg/ml FITC-dextran in a-MEM for 24 hrs at 37° C. and were chased with fresh medium for 2 hrs at the same temperature. RITC-VT binding domain1 B (2-5 µg/ml) was added to the cells in last 1 hr of chase at 37° C. The cells were then washed five times with sterile PBS, fixed in 2% formaldehyde, mounted with DABCO (35) and visualized under incident fluorescent light using a Polyvar fluorescent microscope. Fluorescent images were recorded on Kodak TMAX 400 ASA film.

$^{125}$I-Verotoxin Binding of Intact Cells

Cells were grown on 96 well plates. Media was aspirated, and the cells were washed with PBS (pH 7.4) at room temperature. After equilibrating the cells on ice, 100 µL of ice-cold PBS was added to each well. The radiolabeled toxin was added and allowed to incubate for one hour on ice. Unbound toxin was then washed off with ice cold PBS 3 times. The cells were solublized with 1 ml of 10% SDS added to each well and incubated at 37° C. for 15 minutes and the extracts counted in a gamma counter.

Inhibition of Glycolipid Synthesis

PPMP(1-phenyl-2-hexadecanoylamino-3-morpholino-1-propanol, Matreya Inc., Pleasant Gap, Pa.) is a potent inhibitor of glucosylceramide synthesis (36) and thereby prevents the synthesis of most glycolipids. Experiments extablished that 27 µM PPMP was able to inhibit glycosphingolipid synthesis without inducing cell death. XF-498 astrocytoma and vero cells were then incubated at 37° C. with 27 µM PPMP in the presence and absence of 2 mM butyrate for 6-7 days.

Fluorescence Microscopy

FITC-VT binding domain1 B was prepared as described before (11, 37). Briefly 50 µg of purified VT binding domain1 was dialyzed against borate buffer (50 mM, pH 9.0) overnight. Fluorescein isothiocyanate (FITC,) (10 mg/ml) was added to the dialyzed VT binding domain1B-subunit and allowed to react in the dark for 2 hours at 4° C. and then dialyzed against PBS. The fluorescein-conjugated VT binding domain1B was stored at −70° C. Rhodamine conjugated VT binding domain1B (RITC-VT binding domain1B) was similarly prepared. To determine the subcellular targeting of VT binding domain1 in astrocytoma cells, SF-539 and XF-498 cells grown overnight on glass cover slips were incubated for 1 hr in the presence of 10 µg/ml of FITC-VT binding domain1 B at 37° C. for VT binding domain1 internalization. Following extensive washing with 50 mM PBS, cell were mounted with DABCO and examined under the fluorescence microscope.

Confocal Microscopy

To determine the three dimensional topology of VT binding domain1 subcellular targeting, tumor cells grown on coverslips were incubated in the presence of 10 µg/ml FITC-VT binding domain1B at 37° C. for 1 hr. Following extensive washing with 50 mM PBS, the cells were mounted with DABCO and examined by confocal microscopy using a laser confocal microscope with 40× objective. For double labeling RITC-VT binding domain1B-labeled cells were fixed, permeablized with saposin or 0.1% Triton and treated with rabbit anti ERGIC 53 (kindly provided by Dr H. Hauri, Biozentrum, Basel) or anti BIP (directed against amino acids and not cross reactive with other hsp70s, Santa Cruz Ltd) followed by FITC labeled rabbit antimouse Ig, or FITC-labeled ConA, and washed extensively. For lysosomal double labeling, cells were pretreated with FITC labeled dextran overnight prior to incubation with RITC-VT binding domain1B for 1 hr.

A krypton/argon laser tuned to produce both 488 nm and 565 nm wavelength beams, was used for fluorescein and rhodamine excitation, respectively. The dual filter block, K1K2 and allowed the simultaneous monitoring of the fluorescein and rhodamine emission. The signals were recorded by optical sections of 1 µm thickness. Diaphragm and fluorescence detection level were adjusted in order to avoid any cross-emission from two channel (FITC and RITC). Pictures were recorded with a Kalman filter (average of six images) and transferred to Kodak T-max 400 film. Computational analysis of the digital image allowed precise identification of double labeled structures.

Example 2

RME of a Labeled Hybrid VT Binding Domain Moiety

Subcellular Targeting of VT Binding Domain1B in Astrocytoma Cell Lines

The intracellular routing of VT binding domain1, following RME, was monitored in SF-539 and XF-498 cells, using FITC-labeled B subunit. Similar results were obtained using FITC-VT binding domain1 (data not shown).

The pattern of FITC-VT binding domain1 B localization was completely distinct in the SF-539 and XF-498 astrocytoma cell lines, despite comparable Gb3 content and cell surface binding at 4° C. In the more VT binding domain sensitive SF-539 cells, at 37° C., intracellular FITC-VT binding domain1-B accumulated around the nucleus and apparently within the nucleus. However, the intracellular localization of FITC-VT binding domain1-B in XF-498 cells was in a juxtanuclear location, consistent with Golgi localization. Double labeling confocal microscopy verified the targeting of VT binding domain1B to the the nuclear envelope/ER and nucleus in SF-539 cells. In SF-539 cells, RITC-B also colocalized with anti BIP (GRP 78), a marker for the ER(41) as a ring around the nucleus. The punctate staining for VT binding domain1B and BIP for the most part was coincident, however some BIP staining showed no corresponding toxin localization and vice versa. The latter result is likely due to VT binding domain1B localization in part, in intermediate compartment vesicles (between Golgi and ER) (42). In addition, intranuclear staining is clearly seen for VT binding domain1B but not for BIP. Staining for ERGIC 53, a marker of the intermediate compartment vesicles in part, colocalized with VT binding domain1B staining. In contrast, no nuclear staining was seen for XF-498. Double labeling confocal microscopy showed that the juxtanuclear structure labeled in XF 498 cells was colocalized with Con A labeled Golgi. VT binding domain1B was restricted to the Golgi and did not localize with the additional Con A staining of the ER around the nucleus.

A degree of colocalization of RITC-labeled VT binding domain1B with FITC-dextran (lysosomal marker) was observed in XF-498 cells suggesting that the toxin is internalized through lysosomal/endosomal vesicles in these cells. In SF-539 cells (and butyrate-treated XF-498 cells-not shown) FITC-dextran was not colocalized with any RITC-VT binding domain1B.

Confocal microscopy shows that FITC-VT binding domain1-B was differentially targeted in SKVLB and SKOV3 cells. In SKVLB, cells the internalized toxin is found within the nuclear membrane/ER and nucleus, whereas in SKOV3 cells, the majority of intracellular toxin is in a juxtanuclear location, consistent with Golgi targeting. Thus, intracellular VT binding domain1B is localized in SKVLB in a manner similar to SF 529 and butyrate treated XF 498 cells, whereas in SKOV3 cells, toxin is localized as in XF 498 cells.

Example 3

Preparation of VT Binding Domain Fusion Protein

Recombinant VT binding domain can be produced in a variety of expression systems. For example, the mature VT binding domain peptide can be expressed as a recombinant glutathione-S-transferase (GST) fusion protein in *E. coli* and the fusion protein can be isolated and characterized. Specifically, as described above, VT binding domain (e.g., VT-B) can be fused to GST and this fusion protein can be expressed in *E. coli* strain PEB 199. As GST is predicted to be 26 kD, the fusion protein is predicted to be about 26 kD in molecular weight greater than VT-B. Expression of the GST-VT binding domain fusion protein in PEB 199 can be induced with IPTG. The recombinant fusion protein can be purified from crude bacterial lysates of the induced PEB 199 strain by affinity chromatography on glutathione beads. Polyacrylamide gel electrophoretic analysis of the proteins purified from the bacterial lysates results in isolation of the fusion protein as a band about 26 kD in molecular weight greater than VT-B.

The preparation and purification of modified VT binding domain having a carboxy-terminal tetrapeptide has been reported (Johannes et al. (1997) *J. Biol. Chem.* 272:19554-19561) by using a pSU108-based plasmid expressing the VT binding domain. Fusion proteins according to the invention can be also be purified and labeled as described therein.

Example 4

Preparation of VT Binding Domain DNA Fusion Molecule

Construction of VT1 B subunit λ Cro Fusion Proteins for Transfer of Specific DNA Sequences into the Cell Nucleus.

λ Cro is a 66 amino acid helix-turn-helix DNA-biding protein from bacteriophage λ. This protein binds as a dimer to a 17 base pair λ. operator sequence and acts as a transcription repressor. A stable monomeric form of λ. Cro has been designed which exhibits similar structure to wild-type Cro although with reduced DNA binding capacity (e.g., Mossing and Sauer, *Science* (1990) 250 (4988):1712-5).

To construct the VT1B-Cro fusion protein, the complete wild-type λ. Cro coding sequence from plasmid pUCroRX (gift of M. Mossing, University of Notre Dame, Ind.) is inserted downstream and in frame with the complete VT1 B sequence in plasmid pJLB120 (e.g., Ramotar, et al., *Biochem. J.* (1990) 272 (3): 805-11). pJLB120 is a derivative of the pKK223-3 *E. coli* expression vector. The stop codon in VT1B is eliminated and replaced with a short linker sequence coding for 6-12 hydrophilic residues. This enables both VT1B subunit and Cro domains to exhibit proper folding and molecular interactions. VT1B-Cro is expressed in *E. coli*, and affinity purified by binding to $Gb_3$. To reconstitute fusion protein-DNA binding, the VT1B-Cro fusion protein is incubated with purified (or in vitro translated) wild-type λ. Cro, then this complex is allowed to bind DNA fragments containing λ. operator sequences derived from plasmid ptacλ.1 (e.g., Mossing et al., *Methods Enzymol.* (1991) 208: 604-19).

Alternatively, the fusion protein is constructed as described above, except the wild-type Cro sequence will be replaced with the engineered Cro monomer sequence from plasmid pUCro.mDG (e.g., Mossing and Sauer, *Science* (1990) 250 (4988):1712-5). Purified VT1B-fusion protein is incubated with DNA fragments containing the λ. operator and tested for DNA binding by Electrophoretic Mobility Shift Assay or by DNase I analysis.

The fusion protein constructed as above can be bound to a DNA for which it is selective, and thereby be used to transport the DNA into a cell by receptor-mediated endocytosis.

Example 5

Preparation of a VT-B/Polylysine Hybrid Compound

Commercially-available polylysine (MW1-4000) was activated using EDC (1-ethyl-3(3-dimethylaminopropyl) carbodiimide in the presence of N-hydroxysuccinimide, using the method of Grabarek and Gergely ("Zero Length Crosslinking Procedures with the use of Active Esters" Analytical Biochemistry 185:131-134,1990). The resulting succinimidyl ester was then reacted with the verotoxin 1

B-subunit (purified as described supra), in 0.1 M MES buffer, 0.5M NaCl, pH 6.0, for one hour at room temperature. Crosslinking was monitored by Tricine-SDS-PAGE (polyacrylamide gel eletrophoresis). The PAGE analysis showed the presence of higher molecular weight bands, corresponding to the VT-B/polylysine conjugate.

The VT-B/polylysine conjugate (hybrid compound) is purified by routine methods and is then used complex with a DNA. The hybrid molecule/DNA complex can then be administered to a cell (or to a living subject) to deliver the DNA to the cell.

REFERENCES

1. Sandvig, K., O. Garred, P. K. Holm and B. van Deurs. 1993. Endocytosis and intracellular transport of protein toxins., *Biochem Soc Transact,* 21, 707.
2. Olsnes, S., B. van Deurs and K. Sandvig. 1993. Protein toxins acting on intracellular targets: cellular uptake and translocation to the cytosol, *Med Microbiol Immunol,* 182, 51.
3. Endo, Y., K. Tsurugi, T. Yutsudo, Y. Takeda, K. Ogasawara and K. Igarashi. 1988. Site of the action of a vero toxin (VT binding domain2) from *Escherichia coli* O157:H7 and a Shiga toxin on eukaryotic ribosomes, *Eur J Biochem,* 171, 45.
4. Saxena, S. K., A. D. O'Brien and E. J. Ackerman. 1989. Shiga toxin, Shiga-like toxin II variant, and ricin are all single-site RNA N-glycosidases of 28 S RNA when microinjected into *Xenopus* oocytes, *J Biol Chem,* 264, 596.
5. Mangeney, M., C. A. Lingwood, B. Caillou, S. Taga, T. Tursz and J. Wiels. 1993. Apoptosis induced in Burkitt's lymphoma cells via Gb3/CD77, a glycolipid antigen., *Cancer Res,* 53, 5314.
6. Arab, S., M. Murakami, P. Dirks, B. Boyd, S. Hubbard, C. Lingwood and J. Rutka. submitted. Verotoxins inhibit the growth of and induce apotosis in human astrocytoma cells.,
7. Inward, C. D., J. Williams, I. Chant, J. Crocker, D. V. Milford, P. E. Rose and C. M. Taylor. 1995. Verocytotoxin-1 induces apoptosis in vero cells, *J Infect,* 30, 213.
8. Griffin, P. M. 1995. *Escherichia coli* O157:H7 and other enterohemorrhagic *Escherichia coli*. In Infections of the Gastrointestinal Tract, M. J. Blaser, P. D. Smith, J. I. Ravdin, H. B. Greenberg and R. L. Guerrant, Raven Press, Ltd., New York, 739.
9. Rowe, P., E. Orrbine, G. Wells and P. McLaine. 1991. Epidemiology of the hemolytic-uremic syndrome in Canadian children from 1986-1988, *J Pediat,* 119, 218.
10. Gannon, V. P. J. and C. L. Gyles. 1990. Characteristics of the Shiga-like toxin produced by *Escherichia coli* associated with porcine edema disease, *Vet Microbiol,* 89.
11. Khine, A. A. and C. A. Lingwood. 1994. Capping and receptor mediated endocytosis of cell bound verotoxin (Shiga-like toxin) 1; Chemical identification of an amino acid in the B subunit necessary for efficient receptor glycolipid binding and cellular internalization., *J Cell Physiol,* 161, 319.
12. Sandvig, K., K. Prydz, M. Ryd and B. van Deurs. 1991. Endocytosis and intracellular transport of the glycolipid-binding ligand Shiga toxin in polarized MDCK cells, *J Cell Biol,* 113, 553.
13. Sandvig, K., M. Ryd, O. Garred, E. Schweda and P. K. Holm. 1994. Retrograde transport from the Golgi complex to the ER of both Shiga toxin and the nontoxic Shiga B-fragment is regulated by butyric acid and cAMP, *J Cell Biol,* 126, 53.
14. Sandvig, K. and B. Van Deurs. 1996. Endocytosis, intracellular transport, and cytotroxic action of Shiga toxin and ricin., *Physiol Rev,* 76, 949.
15. Pellizzari, A., H. Pang and C. A. Lingwood. 1992. Binding of verocytotoxin 1 to its receptor is influenced by differences in receptor fatty acid content, *Biochem,* 31, 1363.
16. Kiarash, A., B. Boyd and C. A. Lingwood. 1994. Glycosphingolipid receptor function is modified by fatty acid content: Verotoxin 1 and Verotoxin 2c preferentially recognize different globotriaosyl ceramide fatty acid homologues, *J Biol Chem,* 269, 11138.
17. Arab, S. and C. A. Lingwood. 1996. Influence of phospholipid chain length on verotoxin/globotriaosyl ceramide binding in model membranes: comparison of a surface bilayer film and liposomes, *Glycoconj J,* 13, 159.
18. Nyholm, P. -G., G. Magnusson and C. Lingwood. 1996. Two distinct binding sites for globotriaosyl ceramide on verotoxins: molecular modelling and confirmation by analogue studies and a new glycolipid receptor for all verotoxins, *Chem Biol,* 3, 263.
19. Arab, S., A. Khine, J. Rutka, S. Grinstein and C. Lingwood. 1995. Globotriaosyl ceramide-mediated intracellular targetting of verotoxin. Retrograde transport to the nucleus and beyond, *Glycoconj J,* 24, 499.
20. Lingwood, C. A. 1996. Aglycone Modulation of Glycolipid Receptor Function, *Glycoconj J,* 13, 495.
21. Sandvig, K., O. Garred, K. Prydz, J. Kozlov, S. Hansen and B. van Deurs. 1992. Retrograde transport of endocytosed Shiga toxin to the endoplasmic reticulum., *Nature,* 358, 510.
22. Farkas-Himsley, H., B. Rosen, R. Hill, S. Arab and C. A. Lingwood. 1995. Bacterial colicin active against tumour cells in vitro and in vivo is verotoxin 1, *Proc Natl Acad Sci,* 92, 6996.
23. Petric, M., M. A. Karmali, S. Richardson and R. Cheung. 1987. Purification and biological properties of *Escherichia coli* verocytotoxin, *FEMS Microbiol Letts,* 41, 63.
24. Ramotar, K., B. Boyd, G. Tyrrell, J. Gariepy, C. A. Lingwood and J. Brunton. 1990. Characterization of Shiga-like toxin 1 B subunit purified from overproducing clones of the SLT-1 B cistron, *Biochem J,* 272, 805.
25. Boulanger, J., M. Huesca, S. Arab and C. A. Lingwood. 1994. Universal method for the facile production of glycolipid/lipid matrices for the affinity purification of binding ligands, *Anal Biochem,* 217, 1.
26. Rutka, J., J. Giblin, H. Hoifodt, D. Dougherty, C. Bell, J. McCullough, R. Davis, C. Wilson and M. Rosenblum. 1986. Establishment and characterization of a cell line from a human gliosarcoma, *Cancer Res,* 46, 5893.
27. Rutka, J. T., J. R. Giblin, D. Y. Dougherty, H. C. Liu, J. R. McCulloch, C. W. Bell, R. S. Stem, C. B. Wilson and M. L. Rosenblum. 1987. Establishment and characterization of five cell lines derived from human malignant gliomas, *Acta Neuropathol* (*Berl*), 75, 92.
28. Ponten, J. and E. MacIntyre. 1986. Long-term culture of normal and neoplastic human glia, *Pathol Microbiol Scand,* 81, 791.
29. Westermark, B., J. Ponten and R. Hugosson. 1973. Determinants for the establishment of permanent tissue culture lines from human gliomas, *Acta Pathol Microbiol Scand,* 81, 791.

30. Bradley, G., M. Naik and V. Ling. 1989. P-glycoprotein expression in multidrug-resistant human ovarian carcinoma cell lines, *Canc Res,* 49, 2790.
31. Kueng, W., E. Silber and U. Eppenberger. 1989. Quantification of cells cultured on 96-well plates, *Anal Biochem,* 182, 16.
32. Boyd, B. and C. A. Lingwood. 1989. Verotoxin receptor glycolipid in human renal tissue, *Nephron,* 51, 207.
33. Boulanger, J., M. Petric, C. A. Lingwood, H. Law, M. Roscoe and M. Karmali. 1990. Neutralization receptor-based immunoassay (NeutrELISA) for detection of neutralizing antibodies to *Escherchia coli* verocytotoxin 1, *J Clin Micro,* 28, 2830.
34. Kim, J. H., A. A. Khine, C. A. Lingwood, W. Furuya, M. F. Manolson and S. Grinstein. 1996. Dynamic measurement of the pH of the Golgi complex in living cells using retrograde transport of the verotoxin receptor, *J Cell Biol,* 134, 1387.
35. Krenik, K. D., G. M. Kephart, K. P. Offord, S. L. Dunnette and G. J. Gleich. 1989. Comparison of antifading agents used in immunofluorescence, *J Immunol Methods,* 117, 91.
36. Inokuchi, J. -I. and N. S. Radin. 1987. Preparation of the active isomer of 1-phenyl-2-decanoylamino-3-morpholino-1-propanol, inhibitor of murine glucocerebroside synthetase, *J Lipid Res,* 28, 565.
37. Lingwood, C. A. 1994. Verotoxin-binding in human renal sections, *Nephron,* 66, 21.
38. Pulczynski, S., A. M. Boesen and O. M. Jensen. 1993. Antibody-induced modulation and intracellular transport of CD10 and CD19 antigens in human B-cell lines: An immunofluorescence and immunoelectron microscopy study., *Blood,* 81, 1549.
39. Stirling, J. W. and P. S. Graff. 1995. Antigen unmasking for immunoelectron microscopy: labeling is improved by treating with sodium ethoxide or sodium metaperiodate, then heating on retrieval medium, *J Histochem Cytochem,* 43, 115.
40. Myher, J. J., A. Kuksis and S. Pind. 1989. Molecular species of glycerolipids and sphingomyelins of human erythrocytes: improved method of analysis, *Lipids,* 24, 396.
41. Haas, I. G. 1994. BiP (GRP78), an essential hsp70 resident protein in the endoplasmic reticulum., *Experientia,* 50, 1012.
42. Kappeler, F., C. Itin, R. Schindler and H. P. Hauri. 1994. A dual role for COOH-terminal lysine residues in pre-Golgi retention and endocytosis of ERGIC-53, *J Biol Chem,* 269, 6279.
43. Louise, C. B., S. A. Kaye, B. Boyd, C. A. Lingwood and T. G. Obrig. 1995. Shiga toxin-associated hemolytic uremic syndrome: Effect of sodium butyrate on sensitivity of human unbilical vein endothelial cells to Shiga toxin, *Infect Immun,* 63, 2765.
44. Keusch, G. T., D. W. K. Acheson, L. Aaldering, J. Erban and M. S. Jacewicz. 1996. Comparison of the effects of Shiga-like toxin 1 cytokine-and butyrate pretreated human umbilical and saphenous vein endothelial cells, *J Infect Dis,* 173, 1164.
45. Abe, A., J. A. Shayman and N. S. Radin. 1996. A novel enzyme that catalyzes the esterification of N-acetylsphingosine, *J Biol Chem,* 271, 14383.
46. Sandvig, K., O. Garred, A. van Helvoort, G. van Meer and B. van Deurs. 1996. Importance of glycolipid synthesis for butyric acid-induced sensitization to Shiga toxin and intracellular sorting of toxin in A431 cells, *Mol Biol Cell,* 7, 1391.
47. Lingwood, C. A., H. Law, S. Richardson, M. Petric, J. L. Brunton, S. DeGrandis and M. Karmali. 1987. Glycolipid binding of purified and recombinant *Escherichia coli*-produced verotoxin in vitro, *J Biol Chem,* 262, 8834.
48. Waddell, T., S. Head, M. Petric, A. Cohen and C. A. Lingwood. 1988. Globotriosyl ceramide is specifically recognized by the *E. coli* verocytotoxin 2, *Biochem Biophys Res Commun,* 152, 674.
49. Boyd, B., Z. Zhiuyan, G. Magnusson and C. A. Lingwood. 1994. Lipid modulation of glycolipid receptor function: Presentation of galactose a1-4 galactose disaccharide for Verotoxin binding in natural and synthetic glycolipids., *Eur J Biochem,* 223, 873.
50. St. Hilaire, P. M., M. K. Boyd and E. J. Toone. 1994. Interaction of the Shiga-like toxin type 1 B-subunit with its carbohydrate receptor, *Biochem,* 33, 14452.
51. Head, S., M. Karmali and C. A. Lingwood. 1991. Preparation of VT binding domain1 and VT binding domain2 hybrid toxins from their purified dissociated subunits: Evidence for B subunit modulation of A subunit function, *J Biol Chem,* 266, 3617.
52. Louise, C. B., T. P. Moran, C. A. Lingwood, P. J. Del Vecchio, D. J. Culp,. and T. G. Obrig. 1995. "Binding of [$^{125}$I] Shiga-like toxin-1 to human endothelial cells: implications for the pathogenesis of Shiga toxin-associated hemolytic uremic syndrome", *Endothelium,* 3, z,900 159.
53. Robinson, L. A., R. M. Hurley, C. A. Lingwood and D. G. Matsell. 1995. "*Escherichia coli* verotoxin binding to human paediatric glomerular mesangial cells", *Ped Nephrol,* 9, 700.
54. Cohen, A., V. Madrid-Marina, Z. Estrov, M. Freedman, C. A. Lingwood and H. -M. Dosch. 1990. Expression of glycolipid receptors to Shiga-like toxin on human B lymphocytes: a mechanism for the failure of long-lived antibody response to dysenteric disease, *Int Immunol,* 2, 1.
55. Jacewicz, M. S., D. W. K. Acheson, M. Mobassaleh, A. Donohue-Rolfe, K. A. Balasubramanian and G. T. Keusch. 1995. Maturational regulation of globotriaosylceramide, the Shiga-like toxin 1 receptor, in cultured human gut epithelial cells, *J Clin Invest,* 96, 1328.
56. Jacewicz, M., H. A. Feldman, A. Donohue-Rolfe, K. A. Balasubramanian and G. T. Keusch. 1989. Pathogenesis of *Shigella* diarrhea. XIV. Analysis of Shiga toxin receptors on cloned HeLa cells., *J Infect Dis,* 159, 881.
57. Eiklid, K. and S. Olsnes. 1980. Interaction of *Shigella* cytotoxin with receptors on sensitive and insensitive cells, *J Recept Res,* 1, 199.
58. Johannes, L., D. Tenza, C. Anthoy and B. Goud. 1997. Retrograde transport of KDEL-bearing B-fragment of Shiga toxin, *J Biol Chem,* 272, 19554.
59. Kim, J. H., L. Johannes, B. Goud, C. Antony, C. A. Lingwood, R. Daneman and S. Grinstein. submitted. "Non-invasive measurement of the pH of the endoplasmic reticulum at rest and during calcium release",
60. Maloney, M. D. and C. A. Lingwood. 1994. CD19 has a potential CD77 (globotriaosyl ceramide)-binding site with sequence similarity to verotoxin B-subunits: Implications of molecular mimicry for B cell adhesion and enterohemorrhagic *Escherichia coli* pathogenesis, *J Exp Med,* 180, 191.
61. Khine, A. A. and C. A. Lingwood. submitted. CD77 Dependent Retrograde Transport of CD19 to the Nuclear Membrane: Functional Relationship between CD77 and CD19 during Germinal Center B-cell Apoptosis., 62. Jans, D. 1994. Nuclear signaling pathways for polypeptide ligands and their membrane receptors?, *FASEB,* 8, 841.
63. Stachowiak, M., P. Maher, E. Mordechai and E. Stachowiak. 1996. Nuclear accumulation of fibroblast growth facto receptors is regulated by multiple signals in adrenal medullary cells., *Mol Biol Cell,* 7, 1299.
64. Gillard, B. K., L. T. Thurman, R. G. Harrell, Y. Capentanaki, M. Saito, R. K. Yu and D. M. Marcus. 1994. Biosynthesis of glycosphingolipids is reduced in the absence of a vimentin; intermediate filament network, *J Cell Science,* 107, 3545.
65. van Helvoort, A., A. Smith, H. Sprong, I. Fritzsche, A. Schinkel, P. Borst and G. van Meer. 1996. MDR1 P-Glycoprotein is a lipid translocase of broad specificity, while MDR3 P-glycoprotein specifically translocates phosphatidyl choline., *Cell,* 87, 507.
66. Lavie, Y., H. Cao, S. L. Bursten, A. E. Giuliano and M. C. Cabot. 1996. Accumulation of glucosylceramides in multidrug-resistant cancer cells, *J Biol Chem,* 271, 19530.
67. Burger, K., P. van der Bijl and G. van Meer. 1996. Topology of sphingolipid galactosyl transferase in ER and Golgi:transbilayer movement of monohexyl sphingolipids is required for higher glycosphingolipid biosynthesis., *J Cell Biol,* 133, 15.
68. Bates, S. E., L. Mickley, Y. Chen, N. Richert, J. Rudick, J. Biedler and A. Fojo. 1989. Expression of a drug resistance gene in human neuroblastoma cell lines:modulation by retenoic acid-induced differentiation., *Moll Cell Biol,* 9, 4337.
69. Bates, S. E., S. J. Currier, M. Alvarez and A. T. Fojo. 1992. Modulation of P-glycoprotein phosphorylation and drug transport by sodium butyrate, *Biochem,* 31, 6366.
70. Arab, S., E. Russel, W. Chapman, B. Rosen and C. Lingwood. in press. Expression of the Verotoxin receptor glycolipid, globotriaosyl ceramide in Ovarian Hyperplasias, *Oncol Res,*
71. Newburg, D., P. Chaturvedi, E. Lopez, S. Devoto, A. Feyad and T. Cleary. 1993. Susceptibilty to hemolytic-uremic syndrome relates to erythrocyte glycosphingolipid patterns., *J Infect Dis,* 168, 476.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A hybrid molecule comprising a first domain and a second domain covalently linked, wherein (a) said first domain comprises a domain which is capable of specific binding to globotriaosylceramide, and wherein said first domain is a verotoxin or a B subunit of verotoxin;

(b) said second domain comprises a nucleic acid.

2. The hybrid molecule of claim 1, wherein the first domain is a verotoxin.

3. The hybrid molecule of claim 1, wherein the first domain is a B subunit of verotoxin.

4. The hybrid molecule of claim 1, wherein the nucleic acid is an antisense nucleic acid.

5. A method for modulating a cell-associated activity, comprising contacting a cell with the hybrid molecule of claim 1 in vitro, such that a cell associated activity is altered relative to the cell-associated activity of the cell in the absence of the hybrid molecule, wherein said nucleic acid modulates said cell-associated activity.

6. A hybrid molecule comprising a first domain and a second domain covalently linked, wherein (a) said first domain comprises a domain which is capable of specific binding to globotriaosylceramide, and wherein said first domain is a verotoxin or a B subunit of verotoxin;

(b) said second domain comprises a polypeptide, wherein said polypeptide is a DNA binding element.

7. The hybrid molecule of claim 6, wherein the first domain is a verotoxin.

8. The hybrid molecule of claim 6, wherein the first domain is a B subunit of verotoxin.

9. A method for modulating a cell-associated activity comprising contacting a cell with the hybrid molecule of claim 6 in vitro, such that a cell associated activity is altered relative to the cell-associated activity of the cell in the absence of the hybrid molecule, wherein said nucleic acid modulates said cell-associated activity.

10. The hybrid molecule of claim 1, wherein said nucleic acid is DNA, RNA, or a DNA/RNA chimeric nucleic acid.

11. The method of claim 5, wherein said cell associated activity is cell growth or replication.

12. The method of claim 5, wherein said cell associated activity is expression of an endogenous or exogenous gene product.

13. The method of claim 9, wherein said cell associated activity is cell growth or replication.

14. The method of claim 9, wherein said cell associated activity is expression of an endogenous or exogenous gene product.

* * * * *